United States Patent
Rosati

(10) Patent No.: US 11,166,853 B2
(45) Date of Patent: Nov. 9, 2021

(54) ABSORBENT ARTICLES COMPRISING NONWOVEN MATERIALS HAVING IMPROVED THERMAL CONDUCTIVITY

(71) Applicant: The Procter & Gamble Company, Cincinnati, OH (US)

(72) Inventor: Rodrigo Rosati, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 498 days.

(21) Appl. No.: 16/149,161

(22) Filed: Oct. 2, 2018

(65) Prior Publication Data

US 2019/0110935 A1    Apr. 18, 2019

Related U.S. Application Data

(60) Provisional application No. 62/571,808, filed on Oct. 13, 2017.

(51) Int. Cl.

| | |
|---|---|
| *A61F 13/15* | (2006.01) |
| *A61F 13/49* | (2006.01) |
| *A61F 13/511* | (2006.01) |
| *A61L 15/18* | (2006.01) |
| *A61F 13/514* | (2006.01) |
| *A61F 13/51* | (2006.01) |
| *A61F 13/84* | (2006.01) |
| *D01F 1/10* | (2006.01) |

(52) U.S. Cl.
CPC .. *A61F 13/15203* (2013.01); *A61F 13/49011* (2013.01); *A61F 13/51* (2013.01); *A61F 13/51121* (2013.01); *A61F 13/51405* (2013.01); *A61F 13/84* (2013.01); *A61L 15/18* (2013.01); *A61F 2013/15284* (2013.01); *A61F 2013/51002* (2013.01); *A61F 2013/51026* (2013.01); *D01F 1/10* (2013.01)

(58) Field of Classification Search
CPC .......... A61F 13/15203; A61F 13/49011; A61F 13/51; A61F 13/51121; A61F 13/51405; A61F 13/84; A61F 2013/15284; A61F 2013/51002; A61F 2013/51026
See application file for complete search history.

(56) References Cited

U.S. PATENT DOCUMENTS

| | | | |
|---|---|---|---|
| 5,628,097 A | 5/1997 | Benson et al. | |
| 6,645,190 B1 | 11/2003 | Olson et al. | |
| 6,761,711 B1 | 7/2004 | Fletcher et al. | |

(Continued)

FOREIGN PATENT DOCUMENTS

| | | | | |
|---|---|---|---|---|
| CA | 2733472 | * | 9/2009 | ............ A61F 13/49 |
| WO | WO9730199 A1 | | 8/1997 | |

(Continued)

OTHER PUBLICATIONS

International Search Report, PCT/US2018/053831, dated Jan. 23, 2019, 11 pages.

*Primary Examiner* — Jacqueline F Stephens
(74) *Attorney, Agent, or Firm* — Brian M. Bolam; Christian M. Best

(57) ABSTRACT

Described herein are nonwoven materials including a plurality of fibers. At least some of the plurality of fibers include a filler. The plurality of fibers have a Thermal Conductivity from about 0.25 W/m/K to about 70 W/m/K.

19 Claims, 21 Drawing Sheets

(56) References Cited

U.S. PATENT DOCUMENTS

| | | |
|---|---|---|
| 6,817,994 B2 | 11/2004 | Popp et al. |
| 6,840,928 B2 | 1/2005 | Datta et al. |
| 6,849,067 B2 | 2/2005 | Fletcher et al. |
| 6,893,426 B1 | 5/2005 | Popp et al. |
| 6,953,452 B2 | 10/2005 | Popp et al. |
| 6,969,377 B2 | 11/2005 | Koele et al. |
| 7,156,833 B2 | 1/2007 | Couture-Dorschner et al. |
| 7,201,744 B2 | 4/2007 | Van Gompel et al. |
| 7,497,851 B2 | 3/2009 | Koele et al. |
| 7,682,349 B2 | 3/2010 | Popp et al. |
| 7,732,039 B2 | 6/2010 | Chakravarty et al. |
| 7,862,550 B2 | 1/2011 | Koele et al. |
| 7,901,393 B2 | 3/2011 | Matsuda et al. |
| 8,007,485 B2 | 8/2011 | Popp et al. |
| 8,114,794 B2 | 2/2012 | Grynaeus et al. |
| 8,361,048 B2 | 1/2013 | Kuen et al. |
| 8,372,052 B2 | 2/2013 | Popp et al. |
| 8,579,876 B2 | 11/2013 | Popp et al. |
| 8,747,379 B2 | 6/2014 | Fletcher et al. |
| 9,382,643 B2 | 7/2016 | Moore et al. |
| 9,421,137 B2 | 8/2016 | LaVon et al. |
| 9,475,034 B2 | 10/2016 | Vincent et al. |
| 9,487,893 B2 | 11/2016 | Moore et al. |
| 9,498,389 B2 | 11/2016 | Trennepohl et al. |
| 9,611,572 B2 | 4/2017 | Moore et al. |
| 9,689,096 B2 | 6/2017 | Berrigan et al. |
| 9,744,083 B2 | 8/2017 | Kim et al. |
| 10,195,092 B2 | 2/2019 | Tally et al. |
| 2003/0118814 A1 | 6/2003 | Workman, Jr. et al. |
| 2003/0119400 A1 | 6/2003 | Beitz et al. |
| 2003/0119402 A1 | 6/2003 | Melius et al. |
| 2003/0119405 A1 | 6/2003 | Abuto et al. |
| 2003/0119413 A1 | 6/2003 | Chakravarty et al. |
| 2004/0204698 A1* | 10/2004 | Zenker .............. A61F 13/49001 604/367 |
| 2005/0148258 A1 | 7/2005 | Chakravarty et al. |
| 2007/0037053 A1 | 2/2007 | Anantharaman |
| 2010/0184348 A1* | 7/2010 | McAmish .............. D04H 3/153 442/417 |
| 2011/0250378 A1 | 10/2011 | Eaton et al. |
| 2013/0037481 A1 | 2/2013 | Lalouch et al. |
| 2013/0211363 A1 | 8/2013 | LaVon et al. |
| 2014/0005020 A1 | 1/2014 | LaVon et al. |
| 2015/0250662 A1 | 9/2015 | Isele et al. |
| 2015/0322604 A1 | 11/2015 | Brunner et al. |
| 2016/0023432 A1 | 1/2016 | Deporter et al. |
| 2016/0074250 A1 | 3/2016 | Strube et al. |
| 2016/0136014 A1 | 5/2016 | Arora et al. |
| 2017/0058442 A1 | 3/2017 | Moore et al. |
| 2017/0258955 A1* | 9/2017 | Lindner ................. A61L 15/42 |

FOREIGN PATENT DOCUMENTS

| | | |
|---|---|---|
| WO | 2015171536 A1 | 11/2015 |
| WO | WO2017152925 A1 | 9/2017 |

* cited by examiner

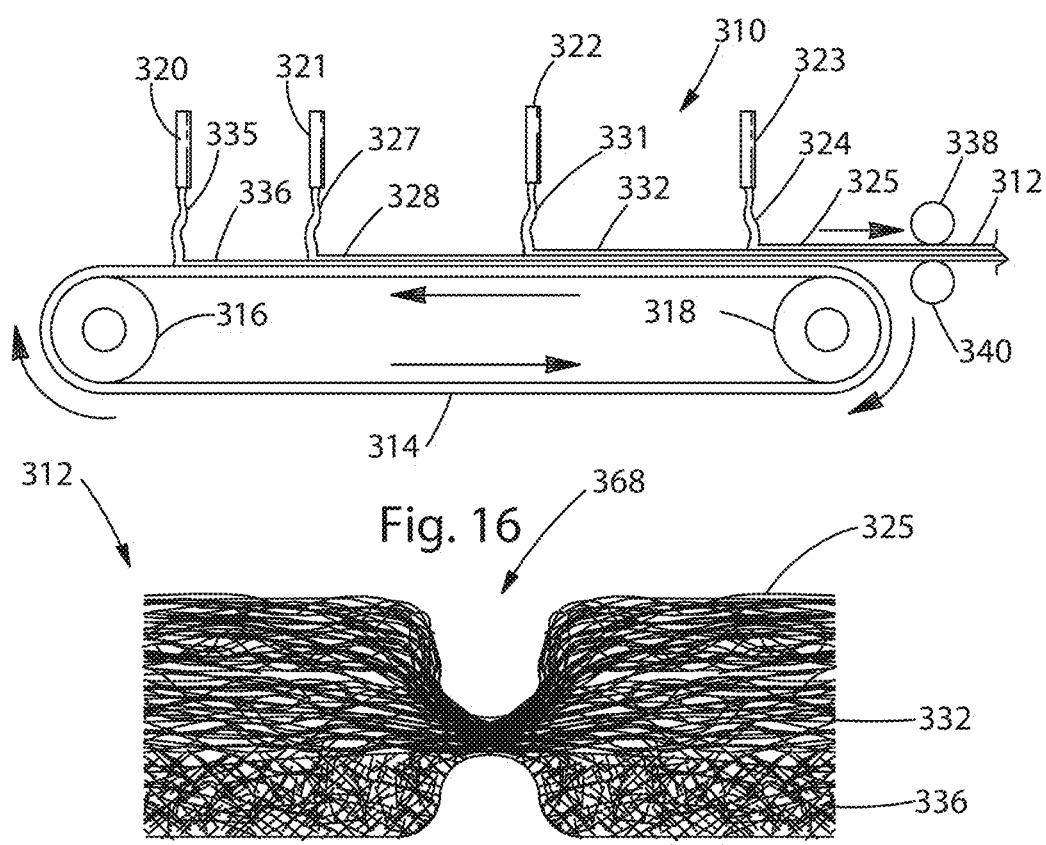
Fig. 16
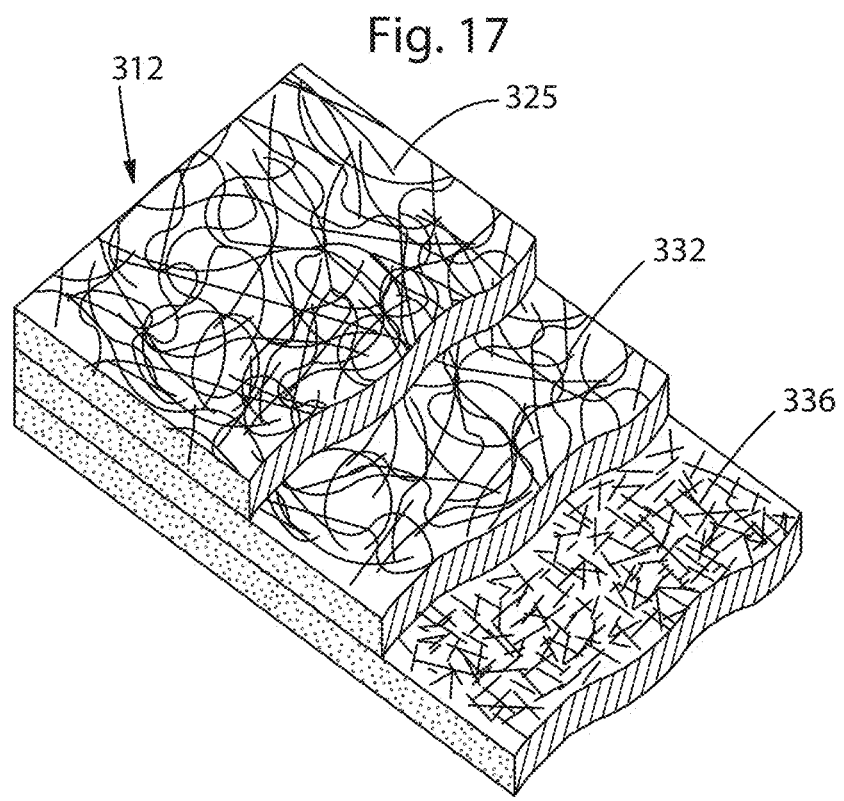
Fig. 17
Fig. 18

ABSORBENT ARTICLES COMPRISING NONWOVEN MATERIALS HAVING IMPROVED THERMAL CONDUCTIVITY

FIELD

Described herein are nonwoven materials having improved thermal conductivity and methods of making the same. Nonwoven materials having improved thermal conductivity are particularly suitable for use in disposable absorbent articles, such as diapers, adult incontinence products, training pants, feminine hygiene products, wipes, dusting substrates, cleaning substrates, and any other suitable consumer products.

BACKGROUND

Nonwoven materials comprising polymeric fibers, such as polyethylene, polypropylene, and polyester, and their bicomponent combinations can be textured and/or apertured. Texturing and/or aperturing processes benefit from pre-heating of the nonwoven material—the increase of temperature allows the nonwoven polymers to deform more easily when undergoing a texturing and/or aperturing process and/or allows the nonwoven polymers to set more firmly at the edges of one or more apertures leaving a cleaner and more stable aperture. When pre-heating the nonwoven material during the texturing and/or aperturing process, as the linear speed of the process increases, the nonwoven material may need to be heated well above the target temperature for softening typical polymers. With conventional nonwoven materials, the high temperature tends to locally melt the fibers and reduce the local softness of the nonwoven material.

Additionally, some nonwoven materials require the fibers to be bonded via the use of heat to create bonds between the fibers to impart mechanical strength to the nonwoven material or for other reasons. This is typically achieved in ovens, both with nonwoven materials made from staple fibers and with nonwoven materials made from spunbond continuous fibers. Such an oven bonding step is often a limiting step as the heat exchange is not as effective at high speeds. Having to limit the speed sometimes results in additional costs for manufacturing the nonwoven materials.

Furthermore when absorbent articles are worn by users, they create an additional thermal resistance, hence limiting the flow of heat away from the body of the user, especially when the environmental temperature is high, for example higher than 30° C. This can lead to thermal discomfort, sweating, and skin health issues in those areas covered by the absorbent article. It would be desirable to reduce the thermal resistance of absorbent articles.

Therefore, there is a need for nonwoven materials which are better capable of exchanging heat when in contact with hot rolls and/or hot air during absorbent article manufacturing processes, as well as to allow a faster heat transmission away from the body of a user.

SUMMARY

Described herein are nonwoven materials having significantly increased thermal conductivity compared to conventional nonwoven materials. These nonwoven materials comprise a plurality of fibers, wherein at least some of the plurality of fibers comprise a filler, and wherein the plurality of fibers have a Thermal Conductivity of at least 0.25 W/m/K.

Nonwoven materials with increased thermal conductivity can be processed at much higher speeds and may even be produced on a diaper line at, for example, about 3-7 meters/second, in contrast to convention nonwoven materials. This can be a great benefit in that the nonwoven materials may not need to be made, wound, and shipped by a nonwoven supplier to an absorbent article manufacturer, reducing shipping costs. In addition, not having to wound the nonwoven materials in order for shipping can be a great benefit because wounding textured nonwoven materials may cause three-dimensional features to compress, potentially resulting in undesirable looks, feel, and/or performance. Last, with fibers having increased thermal conductivity, pre-heating ovens may be made shorter, thereby saving energy and line space.

Also described herein are absorbent articles comprising a nonwoven material, wherein the nonwoven material comprises a plurality of fibers, wherein the plurality of fibers on average comprise from about 3% to about 40%, by weight of the nonwoven material, of a filler selected from the group consisting of boron nitride, graphene, carbon nanotubes, carbon, talc, zinc oxide, and combinations thereof, wherein the plurality of fibers have a Thermal Conductivity of at least 0.25 W/m/K, and wherein the nonwoven material is textured and/or apertured.

Also described herein is a diaper or pant comprising a topsheet, an outer cover, and an absorbent core, wherein the topsheet and/or the outer cover comprise a nonwoven material, wherein the nonwoven material comprises a plurality of fibers, wherein the plurality of fibers have a Thermal Conductivity from about 0.25 W/m/K to about 5 W/m/K, and wherein the nonwoven material is white.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 16 is a schematic diagram of a forming machine used to make a nonwoven material, as described herein;

FIG. 17 is a cross-sectional view of a nonwoven material in a three layer configuration, as described herein;

FIG. 18 is a perspective view of the nonwoven material of FIG. 17 with various portions of nonwoven layers cut away to show the composition of each nonwoven layer, as described herein;

DETAILED DESCRIPTION

Figure 1:
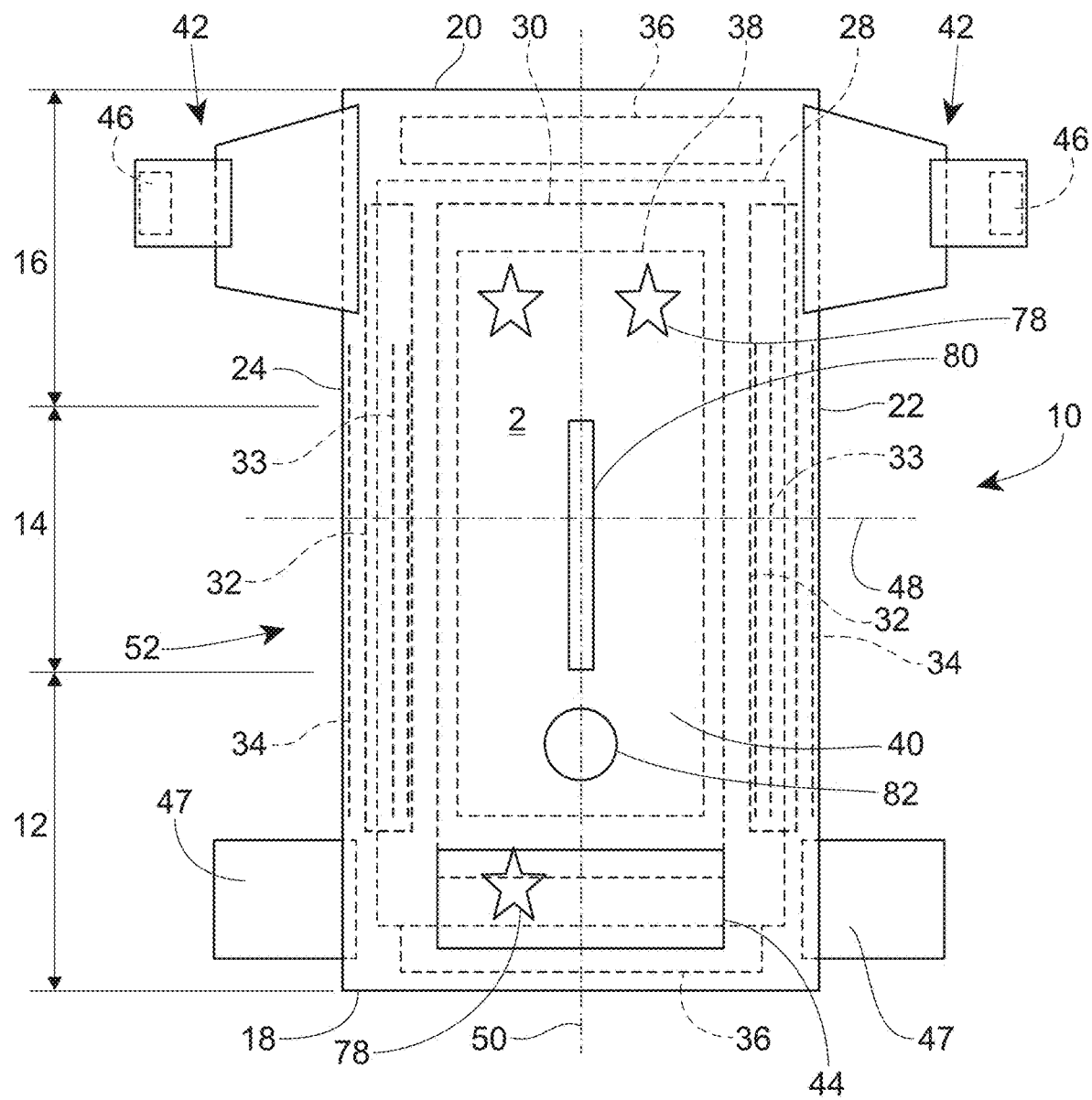
FIG. 1 is a plan view of an example absorbent article in the form of a taped diaper, garment-facing surface facing the viewer, in a flat laid-out state, as described herein.

Various non-limiting forms of the present disclosure will now be described to provide an overall understanding of the principles of the structure, function, manufacture, and use of the nonwoven materials disclosed herein. One or more examples of these non-limiting forms are illustrated in the accompanying drawings. Those of ordinary skill in the art will understand that the nonwoven materials described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "absorbent article" refers to devices which absorb and contain bodily exudates (e.g., BM, urine, blood), and, more specifically, refers to devices which are placed against or in proximity to the body of the wearer to absorb and contain the various bodily exudates discharged from the body. The term absorbent article includes, but is not limited to, diapers, pants, training pants, adult incontinence products, sanitary napkins, tampons, wipes, and liners. The term "absorbent article" may also encompass cleaning or dusting pads or substrates that have some absorbency.

As used herein, the term "thermally conductive fibers" refers to any fiber having a Thermal Conductivity of at least 0.25 W/m/K.

As used herein, the term "elastic" refers to any material that, upon application of a biasing force, can stretch to an elongated length of at least about 110% of its relaxed, original length (i.e., can stretch to 10 percent), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). "Elastic" may refer to a single material, or it may refer to a combination of materials making up a laminate in an article. An elastic material may be incorporated into a laminate which is not elastic, or which is less elastic than one or more of the elastic materials of the laminate.

As used herein, the terms "join", "joined", "joining", "bond", "bonded", "bonding", "attach", "attached", or "attaching" encompass configurations whereby an element is directly secured to another element by affixing the element directly to the other element, and configurations whereby an element is indirectly secured to another element by affixing the element to intermediate member(s) which in turn are affixed to the other element.

As used herein, the term "meltblown", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carded by the high velocity gas stream and are deposited on a collecting surface to form a web of randomly dispersed meltblown fibers.

As used herein, the term "microfibers", refers to small diameter fibers having an average diameter not greater than about 100 microns.

As used herein, the terms "nonwoven material", "nonwoven", or "nonwoven layer" are used in their normal sense and specifically, refers to a web that has a structure of individual fibers or threads which are interlaid, but not in any regular, repeating manner. Nonwoven materials, nonwovens, or nonwoven layers have been, in the past, formed by a variety of processes, such as, for example, meltblowing processes, spunbonding processes and bonded carded web processes.

As used herein, the term "polymer" generally includes, but is not limited to, homopolymers, copolymers, such as, for example, block, graft, random, and alternating copolymers, terpolymer, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "spunbond", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

General Description of an Absorbent Article

Figure 2:
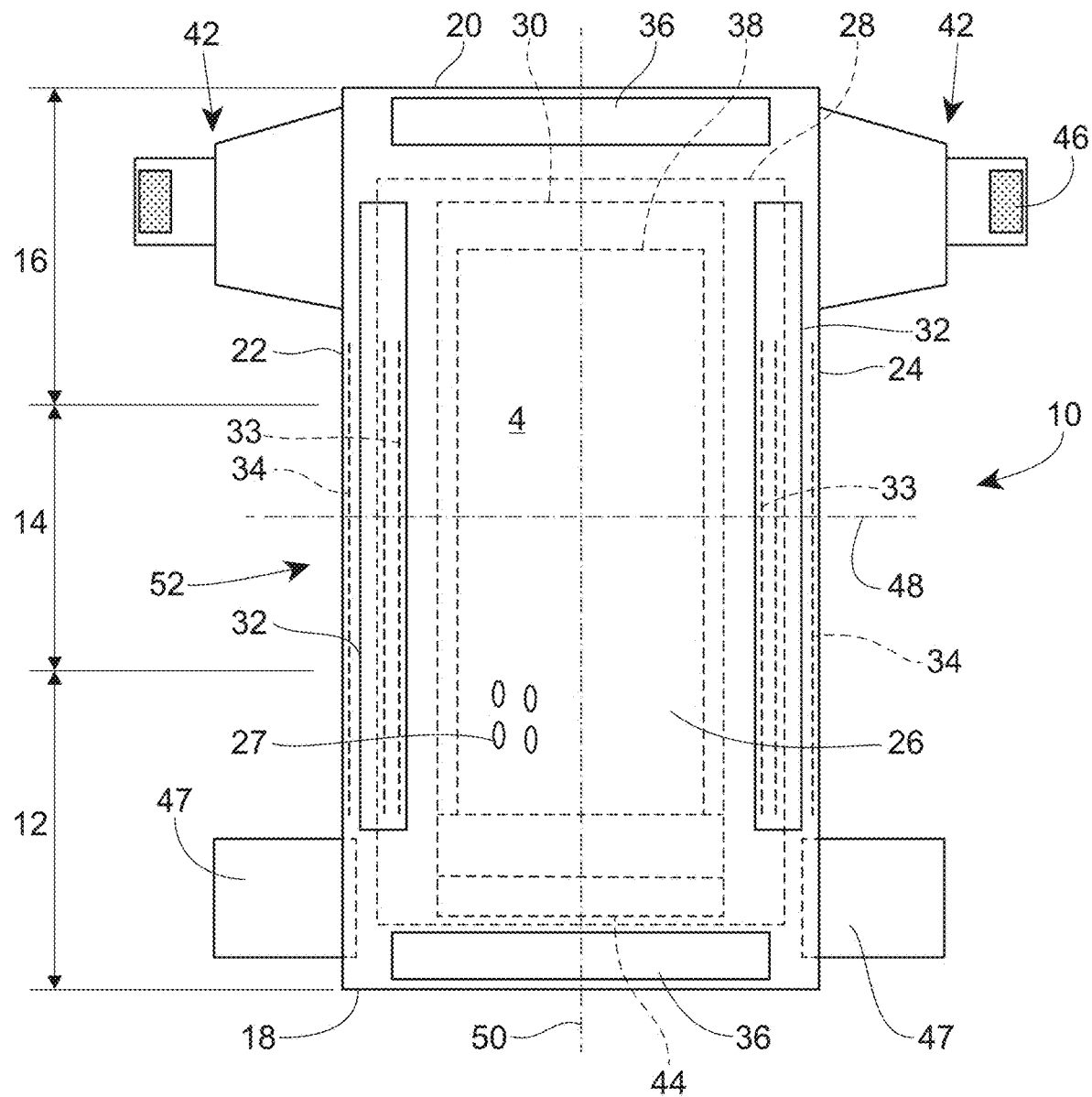
FIG. 2 is a plan view of the example absorbent article of FIG. 1, wearer-facing surface facing the viewer, in a flat laid-out state, as described herein.
Figure 3:
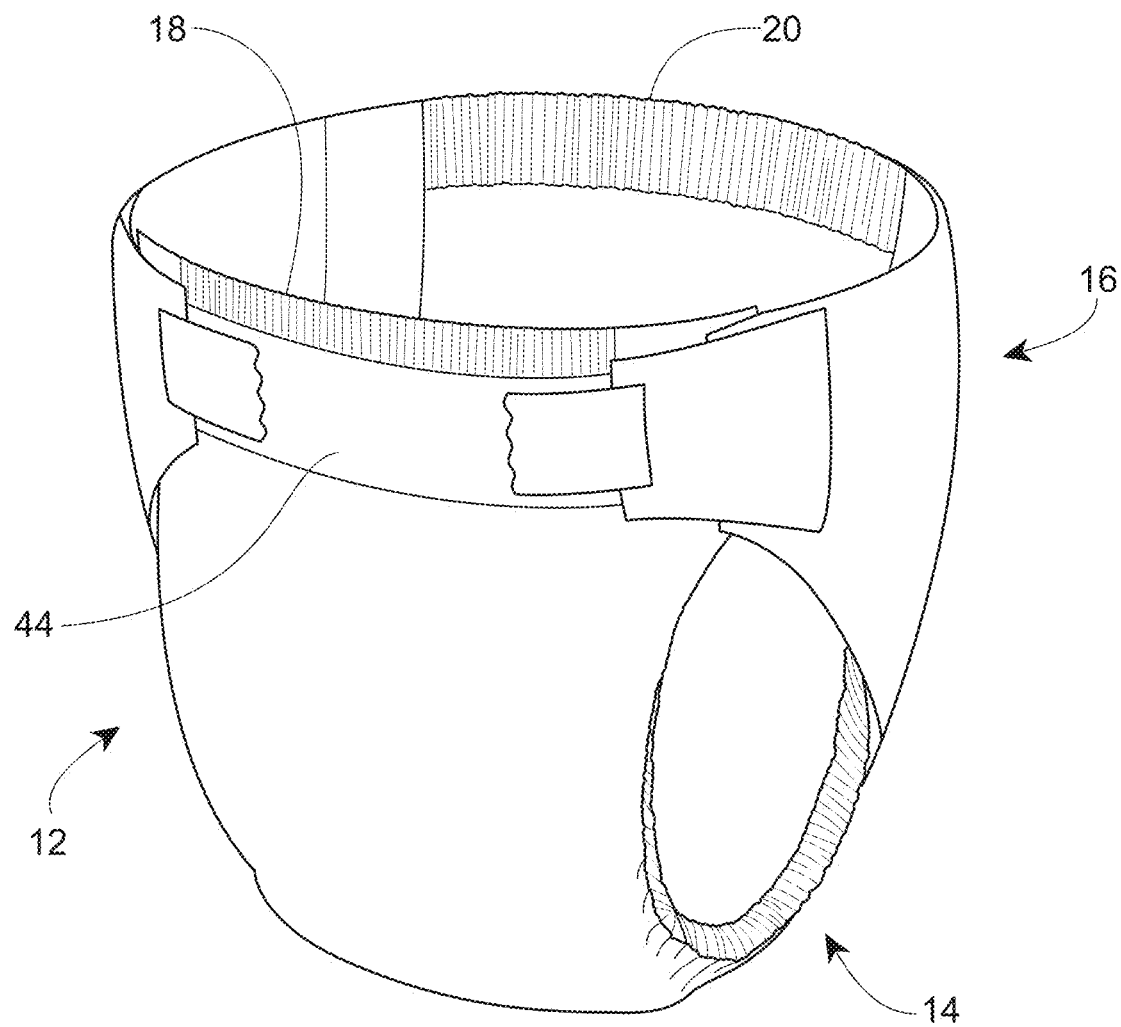
FIG. 3 is a front perspective view of the absorbent article of FIGS. 1 and 2 in a fastened position, as described herein.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
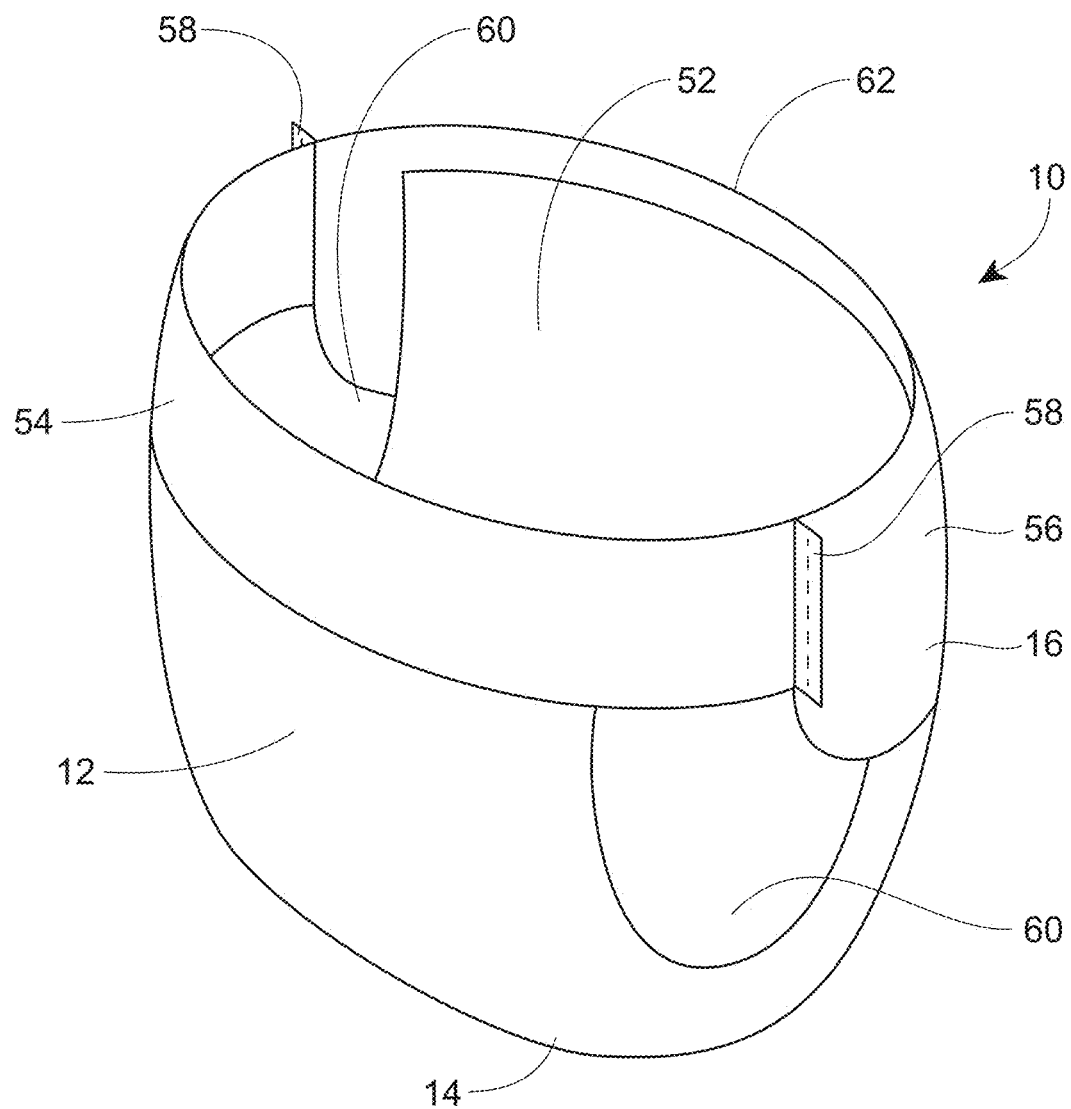
FIG. 4 is a front perspective view of an absorbent article in the form of a pant, as described herein.
Figure 5:
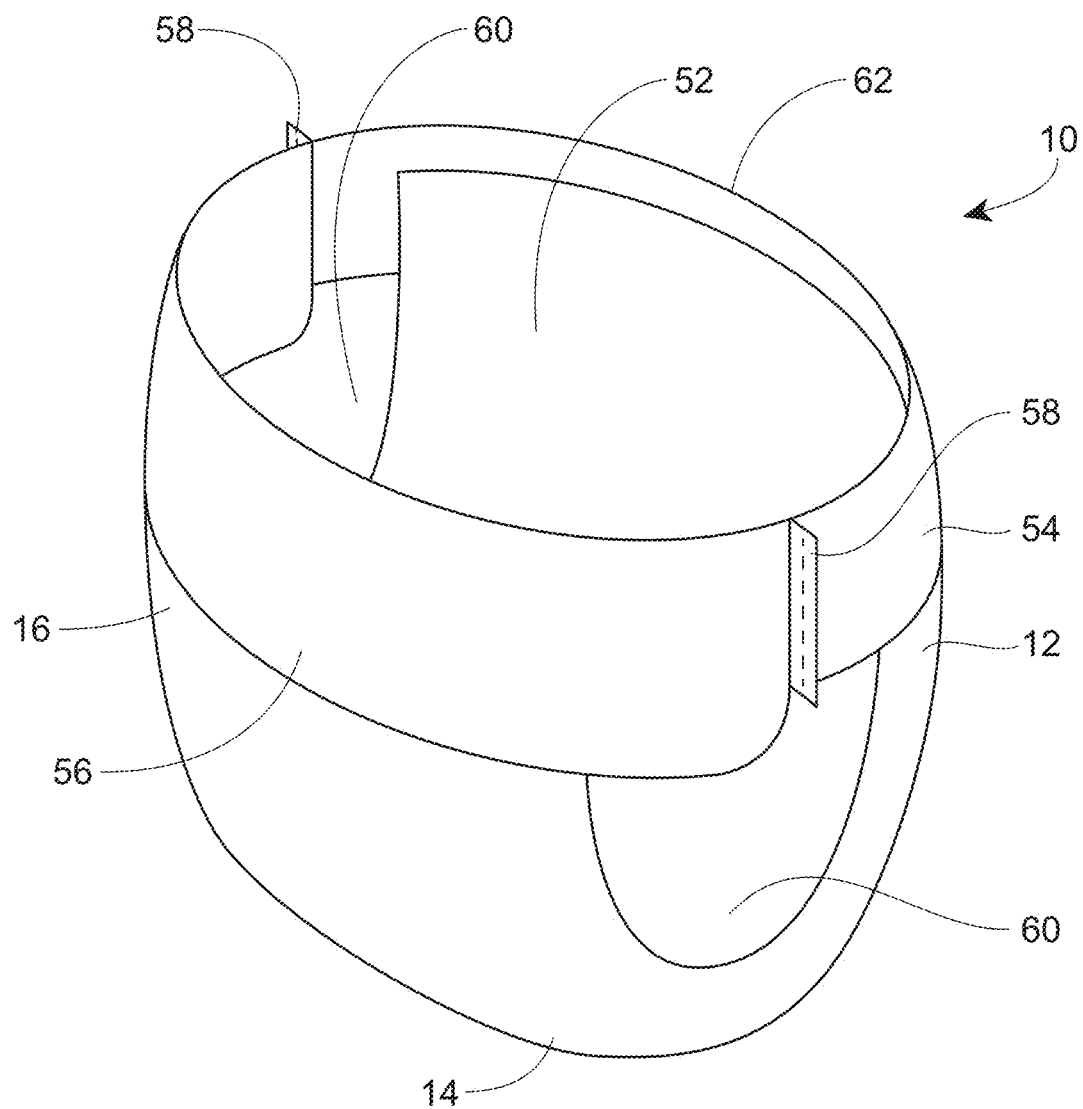
FIG. 5 is a rear perspective view of the absorbent article of FIG. 4, as described herein.
Figure 6:
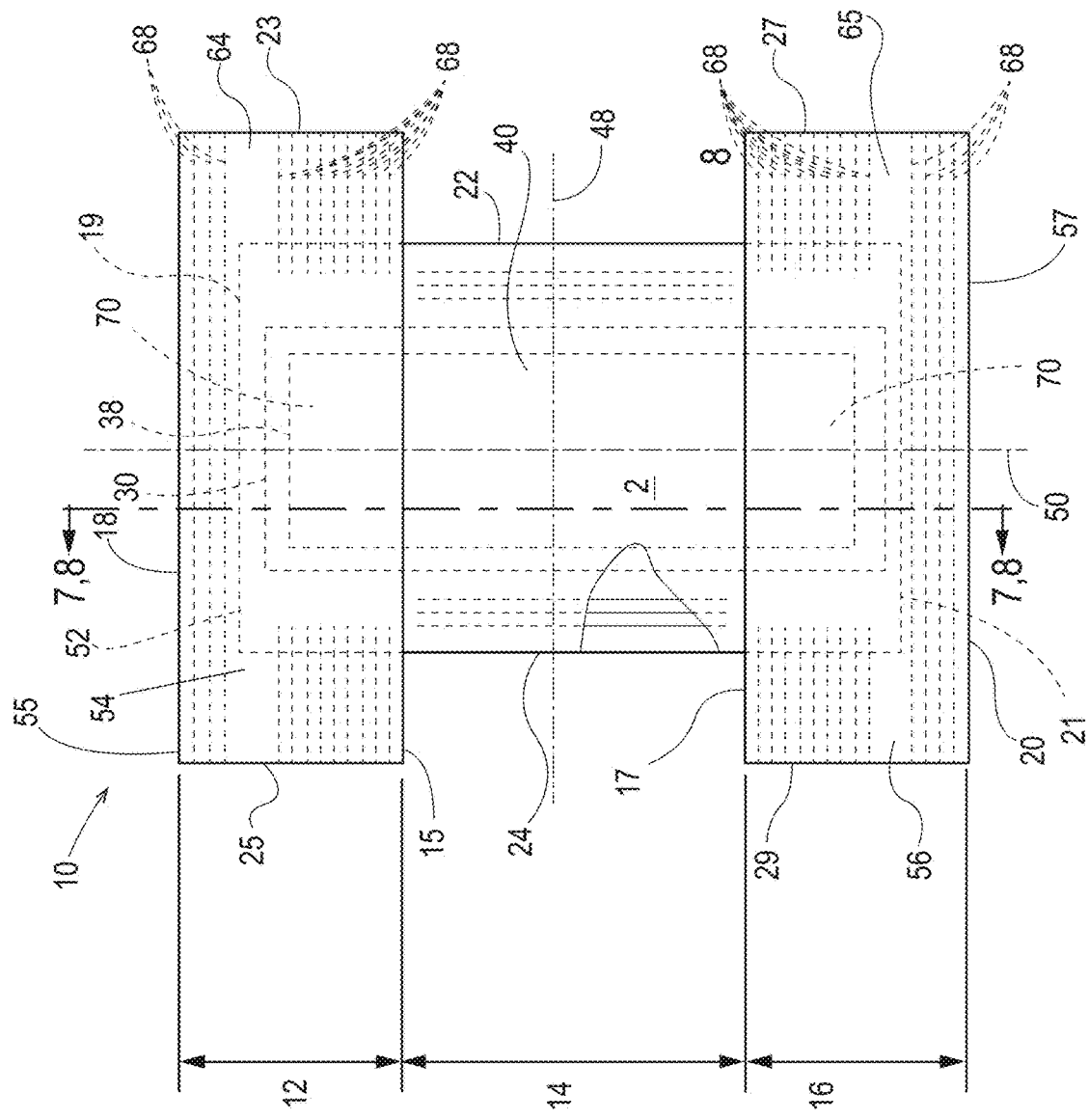
FIG. 6 is a plan view of the absorbent article of FIG. 4, laid flat, with a garment-facing surface facing the viewer, as described herein.
Figure 7:
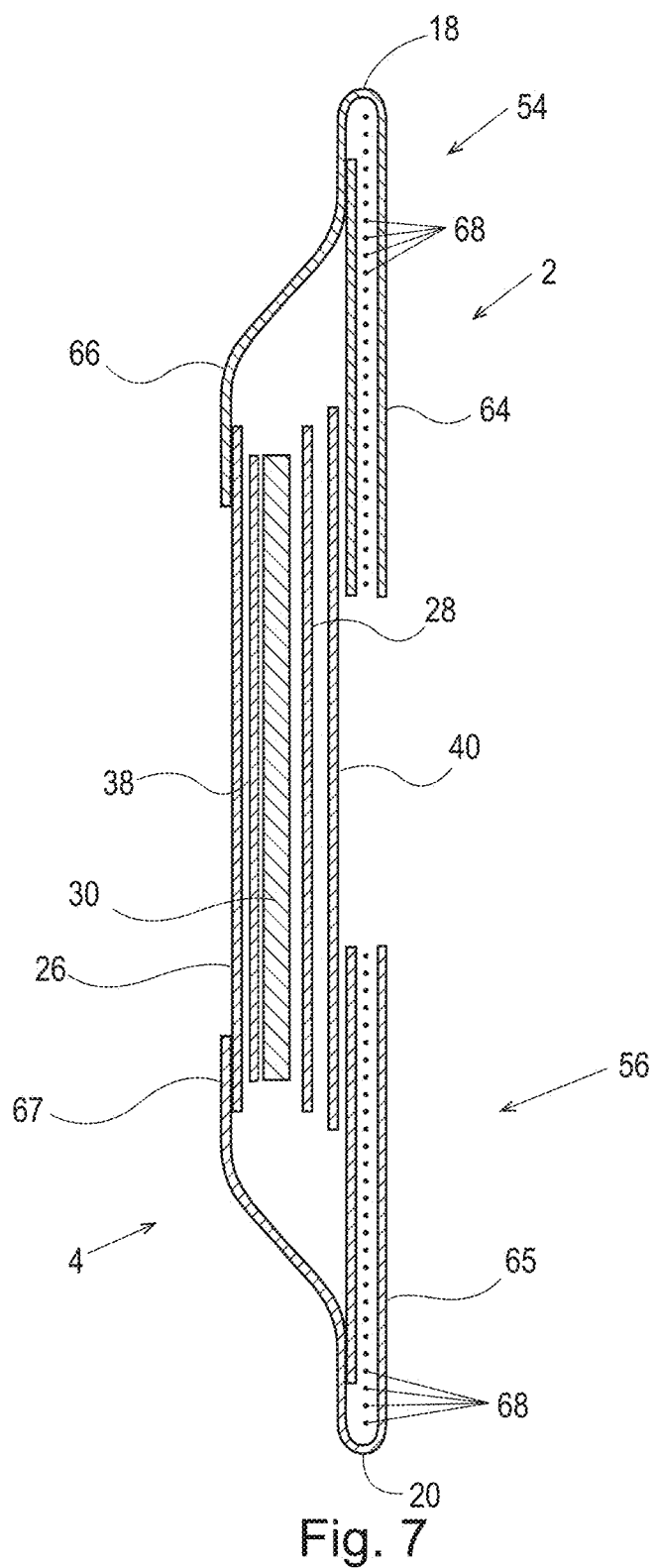
FIG. 7 is a cross-sectional view of the absorbent article taken about line 7-7 of FIG. 6, as described herein.
Figure 8:
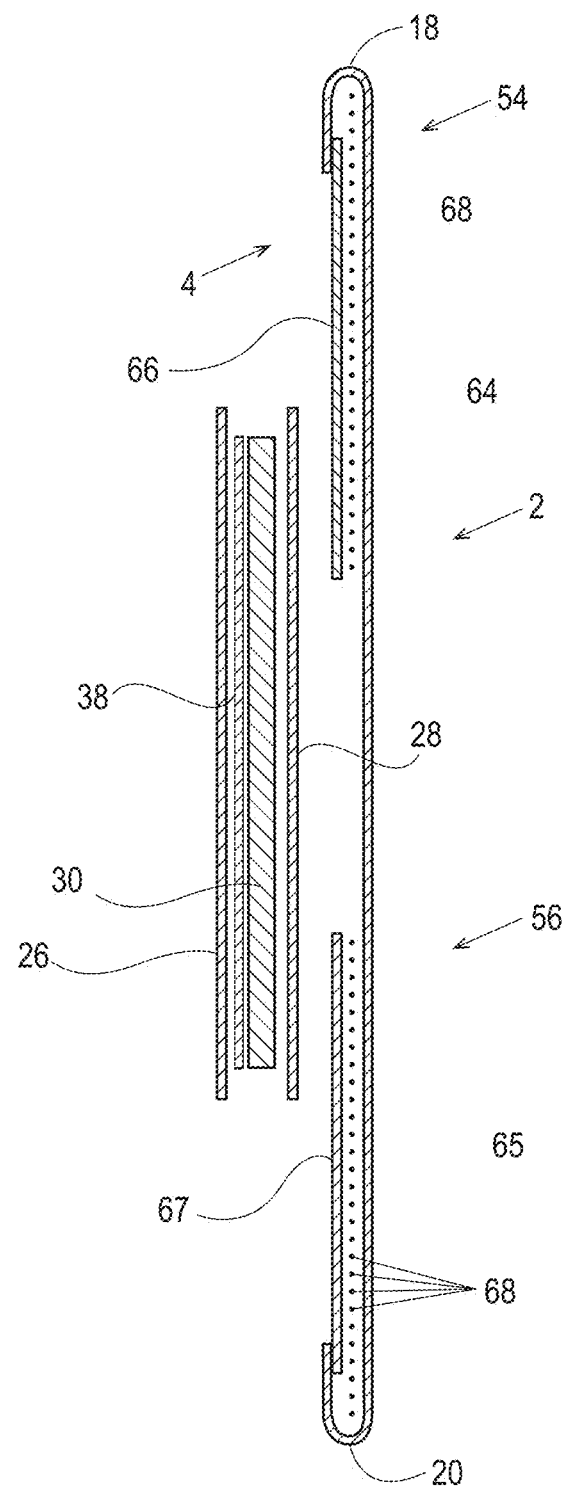
FIG. 8 is a cross-sectional view of the absorbent article taken about line 8-8 of FIG. 6, as described herein.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 27), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

Absorbent Core

Figure 9:
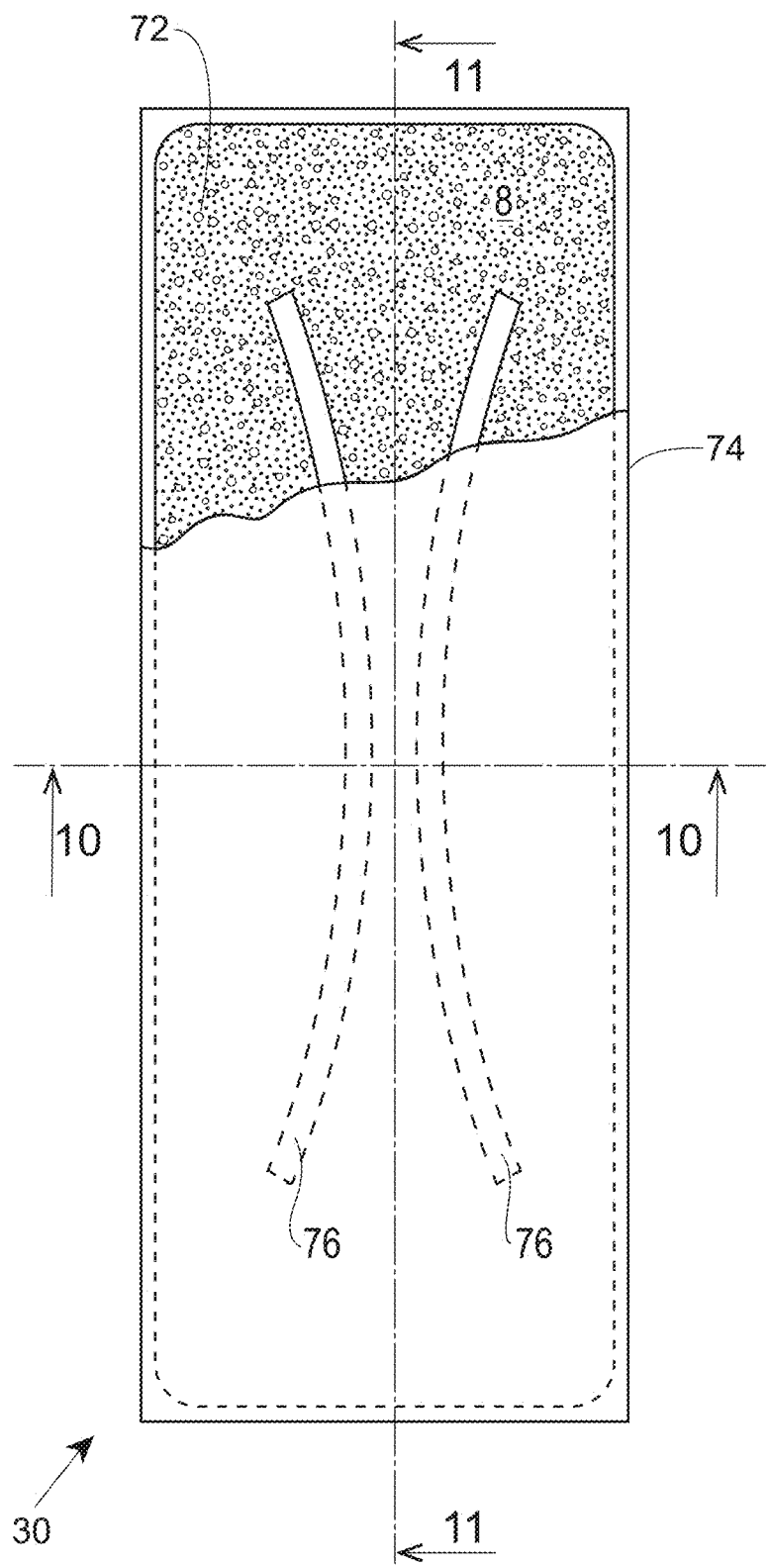
FIG. 9 is a plan view of an example absorbent core or an absorbent article, as described herein.
Figure 10:
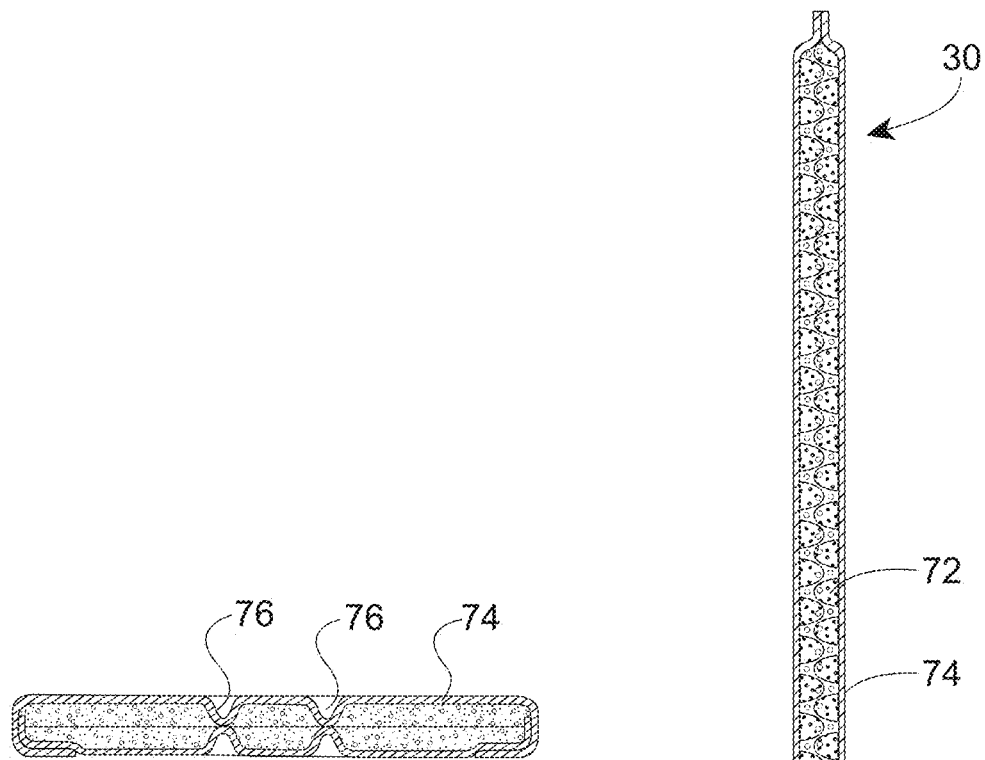
FIG. 10 is a cross-sectional view, taken about line 10-10, of the absorbent core of FIG. 9, as described herein.
Figure 11:
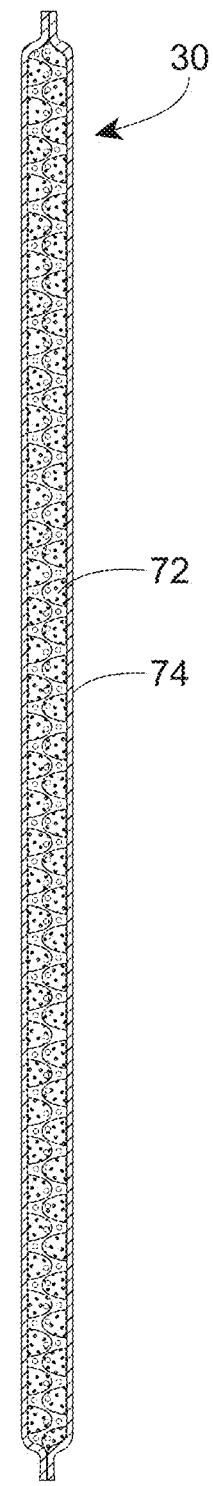
FIG. 11 is a cross-sectional view, taken about line 11-11, of the absorbent core of FIG. 10, as described herein.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Figure 12:
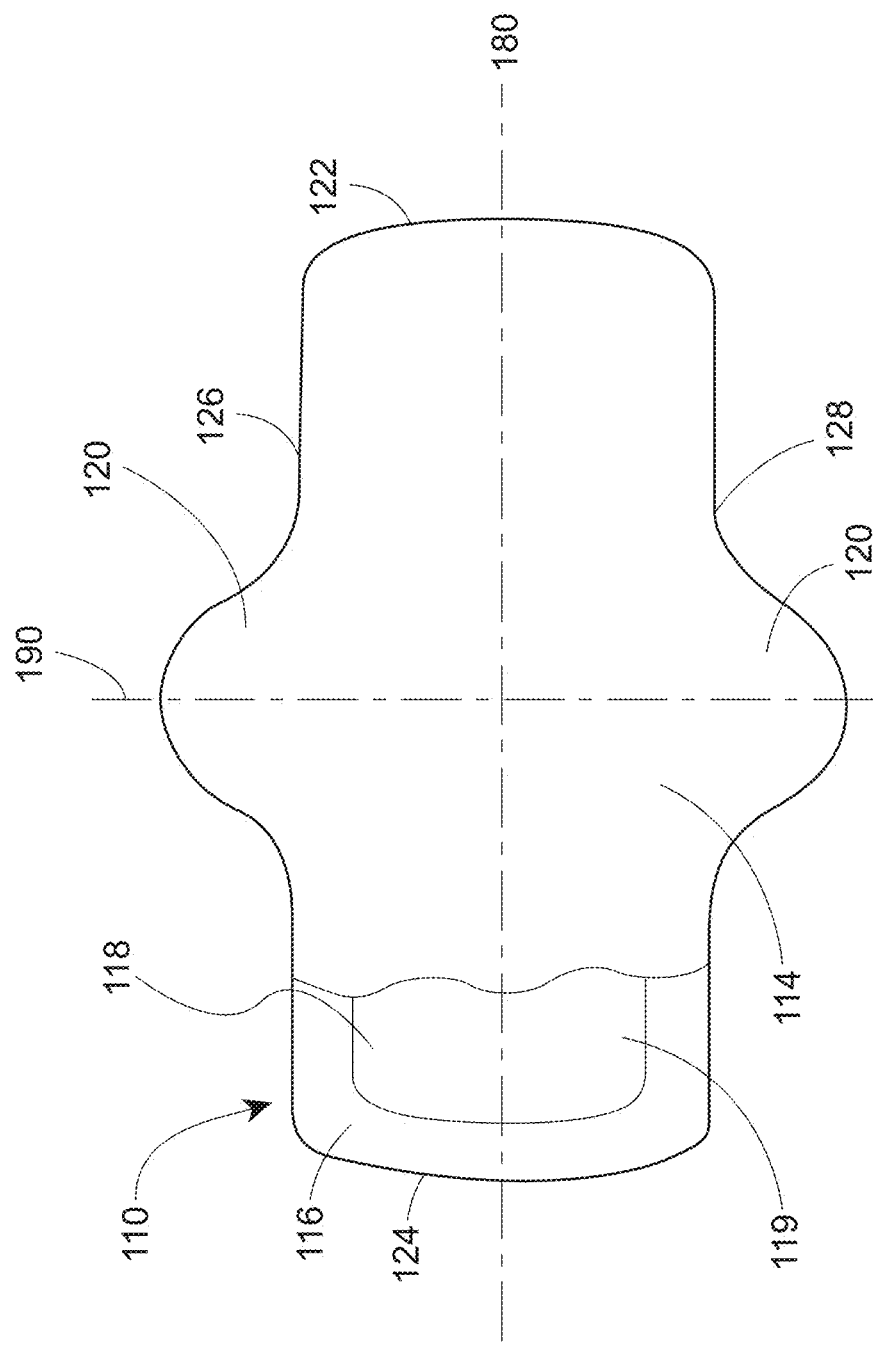
FIG. 12 is a plan view of a sanitary napkin, as described herein.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Examples Cross-Sections of Absorbent Articles

Figure 13:
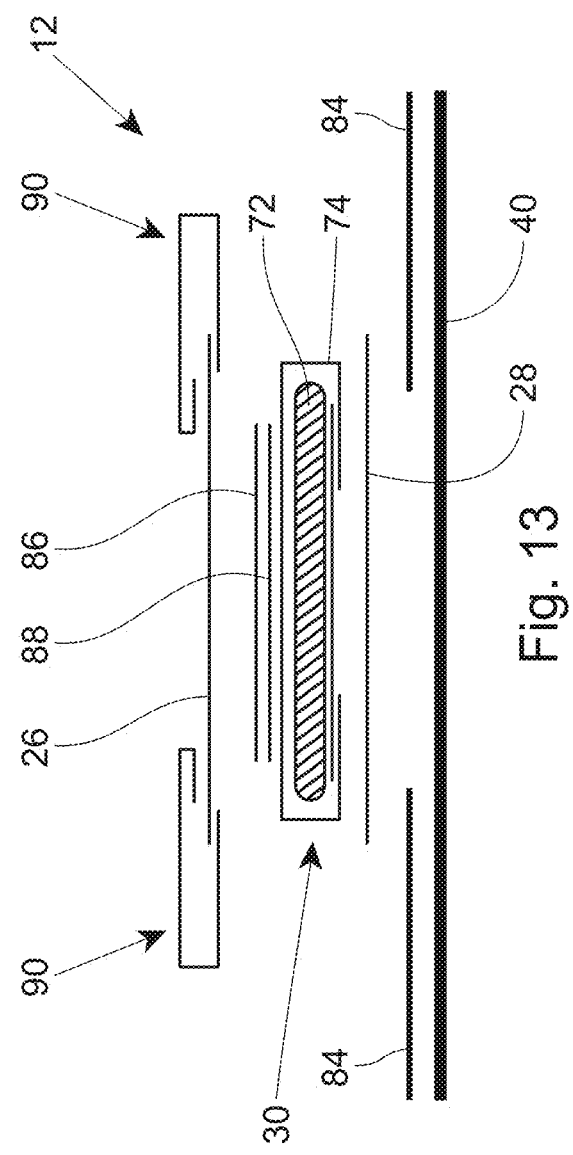
FIG. 13 is an example cross-sectional view taken within a front waist region of an absorbent article, as described herein.
Figure 14:
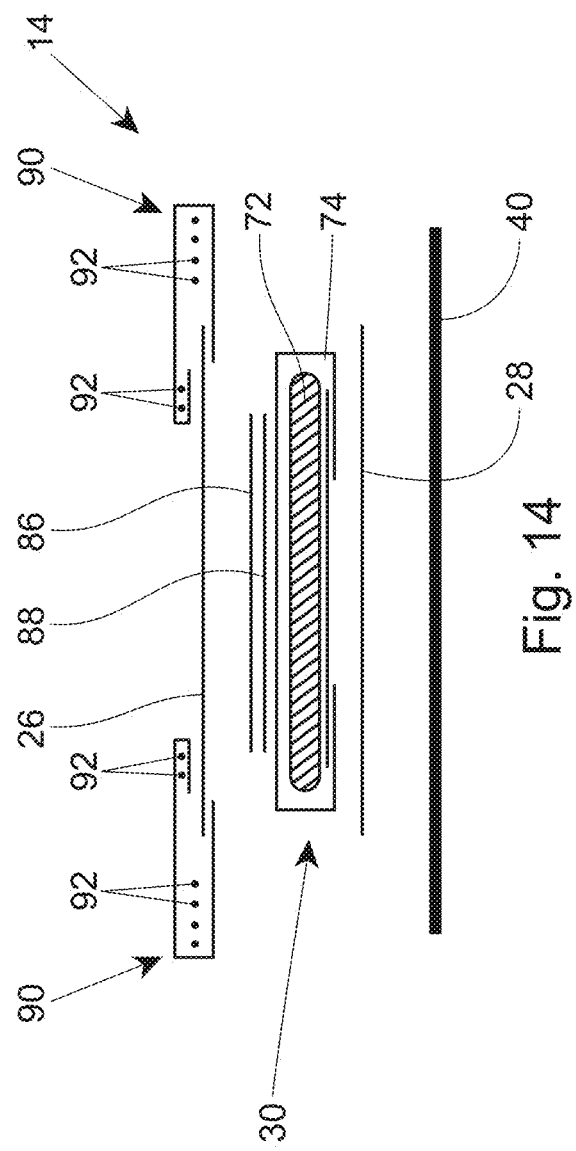
FIG. 14 is an example cross-sectional view taken within a crotch region of an absorbent article, as described herein.
Figure 15:
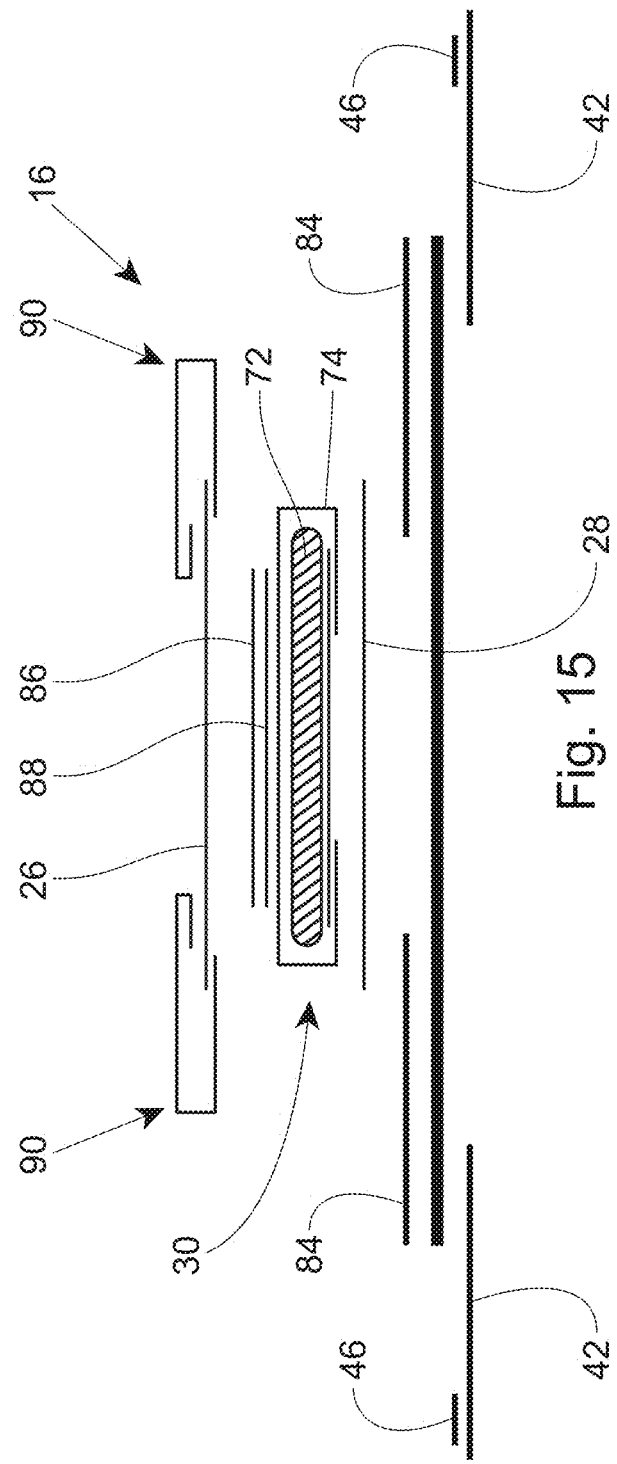
FIG. 15 is an example cross-sectional view taken within a back waist region of an absorbent article, as described herein.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Nonwoven Material

Described herein are nonwoven materials comprising a plurality of fibers, wherein at least some of the plurality of fibers comprise a filler selected from the group consisting of boron nitride, graphene, carbon nanotubes, carbon, talc, zinc oxide, and combinations thereof. The filler may be selected from the group consisting of boron nitride, talc, zinc oxide, magnesium oxide, jade, jadeite, nephrite, mica, phyllosilicates, silicate minerals, clay minerals, and combinations thereof. When the filler is selected, for example, from the group consisting of boron nitride, talc, zinc oxide, and combinations thereof, the nonwoven material may be white. The filler may not contain calcium carbonate and/or the plurality of fibers may not comprise polyester and/or natural fibers, such as pulp, cotton, rayon, etc. The plurality of fibers may comprise only thermoplastic fibers.

The filler may be ImerCare Opaline talc available from Imerys, having a specific surface area of 20 g/m$^2$, according to BET ISO 9277, or the filler may be Boron Nitride powder Typ SCP 1, available from 3M, having a specific surface area of 20 g/m$^2$, according to BET ISO 9277.

The nonwoven material may be made via spinning a compounded polypropylene. The compounded polypropylene may be produced via mixing with a general mixing screw Exxon Achieve 1605 Polypropylene (PP) with ImerCare Opaline talc. A 5% filler loading level may be made at 40 lbs/hour (2 lbs/hour of Opaline and 38 lbs/hour of PP) with a screw speed of 500 RPM. A 15% talc loading level may be made at 40 lbs/hour (6 lbs/hour of Opaline and 34 lbs/hour of PP) with a screw speed of 500 RPM. A 29.4% loading level may be made at 17 lbs/hour (5 lbs/hour of Opaline and 12 lbs/hour of PP) with a screw speed of 500 RPM.

An absorbent article such as a diaper or a pant can comprise the nonwoven material. The nonwoven materials may form part of the topsheet, the outer cover of a diaper, and/or may form any other nonwoven materials in the absorbent article.

The fillers described herein may have a Particle Size Distribution (PSD) D50 from about 0.1 micron to about 10 μm, alternatively less than 1 μm, alternatively less than 0.9 μm, alternatively less than 0.5 μm. Particle Size Distribution (PSD) D50 means that 50% of the sample's volume is smaller than and 50% of a sample's volume is larger than.

The fillers described herein may have a specific surface area, measured according to BET method ISO 9277, of equal or higher than 15 m$^2$/g, alternatively equal or higher than 20 m$^2$/g, alternatively from about 15 m$^2$/g to about 60 m$^2$/g, alternatively from about 15 m$^2$/g to about 50 m$^2$/g, and alternatively from about 20 m$^2$/g to about 45 m$^2$/g.

The fillers described herein may have a lamella shape. By lamella shape, it is meant here that the fillers have a shape similar to a plate or flake, characterized by a high aspect ratio between the major dimension of the plate and the thickness of the plate, such aspect ratio being higher than 5, alternatively higher than 10, alternatively from about 5 to about 150, alternatively from about 10 to about 100, alternatively from about 15 to about 75, and alternatively from about 20 to about 50. The plurality of fibers comprise a plurality of thermally conductive fibers, wherein the plurality of thermally conductive fibers can comprise at least 10%, alternatively at least 15%, and alternatively at least 20% of the filler by weight of the plurality of thermally conductive fibers. Without being bound by theory, at these levels the filler can create a connected network within the plurality of thermally conductive fibers allowing for faster heat transport, or otherwise said, a higher Thermal Conductivity, as described below. Such connected network can be more effective in transferring heat if one or more fillers are chosen with a higher specific surface area and/or with lamella shape.

Alternatively, the plurality of thermally conductive fibers may each comprise from about 10% to about 40%, alternatively from about 15% to about 35%, alternatively from about 10% to about 30%, alternatively from about 20% to about 25%, and alternatively from about 5% to about 20% of the filler by weight of the plurality of thermally conductive fibers, specifically reciting all 0.5% increments within the specified ranges and all ranges formed therein or thereby. Without being bound by theory, the upper limit of the filler in the plurality of thermally conductive fibers may be less than 30%, alternatively less than 20% to avoid problems with the melt spinning process which may impede fiber formation The plurality of fibers may on average comprise from about 1% to about 40%, alternatively from about 2% to about 40%, alternatively from about 3% to about 40%, alternatively from about 4% to about 35%, alternatively from about 5% to about 30%, alternatively from about 6% to about 25%, alternatively from about 7% to about 20%, alternatively from about 8% to about 15%, and alternatively from about 0.5% to about 10% of the filler by weight of the nonwoven material, specifically reciting all 0.5% increments within the specified ranges and all ranges formed therein or thereby.

The fillers described herein may be compounded with a polymer at a processing temperature higher than the polymer melting point. The product of the compounder can be in pellet form, which then can be molten and spun into fibers, which optionally can be cut into staple fibers.

The plurality of fibers may on average comprise from about 70% to about 98%, alternatively from about 70% to about 95%, alternatively from about 75% to about 90%, alternatively from about 85% to about 90%, and alternatively from about 75% to about 80% of the polymer by weight of the nonwoven material. The plurality of thermally conductive fibers may each comprise from about 70% to about 90%, alternatively from about 75% to about 85%, and alternatively from about 75% to about 80% of the polymer by weight of the plurality of thermally conductive fibers.

The polymer may be a polyolefin, and the polyolefin may be selected from the group consisting of polyesters, polypropylenes, polyethylenes, polyethers, polyamides, polyhydroxyalkanoates, polysaccharides, and combinations thereof. More specifically, synthetic fibers may be selected from the group consisting of polyethylene terephthalate, polybutylene terephthalate, poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer, polycaprolactone, polyhydroxyl ether ester, polyhydroxyl ether amide, polyesteramide, polylactic acid, polyhydroxybutyrate, and combinations thereof. Additionally, other synthetic fibers such as rayon, polyethylene, and polypropylene fibers can be used.

The synthetic fibers may be selected from the group consisting of polypropylene, polyethylene, polyester, polyethylene terephthalate, polybutylene terephthalate, polyamide, polylactic acid, and combinations thereof.

Further, the synthetic fibers may be single component fibers (i.e., single synthetic material or a mixture to make up the entire fiber), multicomponent fibers, such as bicomponent fibers (i.e., the fiber is divided into regions, the regions including two or more different synthetic materials or mixtures thereof), and combinations thereof.

The nonwoven may also comprise semi-synthetic fibers made from polymers, specifically hydroxyl polymers. Non-limiting examples of suitable hydroxyl polymers include polyvinyl alcohol, starch, starch derivatives, chitosan, chitosan derivatives, cellulose derivatives such as viscose, gums, arabinans, galactans, and combinations thereof.

The plurality of fibers and/or the plurality of thermally conductive fibers may have a Thermal Conductivity of at least 0.25 W/m/K, alternatively at least 0.3 W/m/K, alternatively at least 0.35 W/m/K, alternatively at least 0.4 W/m/K, and alternatively at least 0.45 W/m/K. Alternatively, the plurality of fibers and/or the plurality of thermally conductive fibers may have a Thermal Conductivity from about 0.1 W/m/K to about 5 W/m/K, alternatively from about 0.1 W/m/K to about 1 W/m/K, alternatively from about 0.25 W/m/K to about 0.5 W/m/K, alternatively from about 0.25 W/m/K to about 10 W/m/K, alternatively from about 0.3 W/m/K to about 9 W/m/K, alternatively from about 0.4 W/m/K to about 8 W/m/K, alternatively from about 0.5 W/m/K to about 7 W/m/K, alternatively from about 0.6 W/m/K to about 6 W/m/K, alternatively from about 0.7 W/m/K to about 5 W/m/K, alternatively from about 0.8 W/m/K to about 4 W/m/K, alternatively from about 0.9 W/m/K to about 3 W/m/K, and alternatively from about 1 W/m/K to about 2 W/m/K, specifically reciting all 0.05 W/m/K increments within the specified ranges and all ranges formed therein or thereby.

The plurality of fibers and/or the plurality of thermally conductive fibers may have a Heat Capacity from about 0.5 J/g/K to about 2 J/g/K, alternatively from about 0.5 J/g/K to about 1.7 J/g/K, alternatively from about 0.5 J/g/K to about 1.6 J/g/K, alternatively from about 0.5 J/g/K to about 1.5 J/g/K, alternatively from about 0.5 J/g/K to about 1.4 J/g/K, alternatively from about 0.6 J/g/K to about 1.3 J/g/K, alternatively from about 0.7 J/g/K to about 1.2 J/g/K, alternatively from about 0.8 J/g/K to about 1.1 J/g/K, and alternatively from about 0.9 J/g/K to about 1.0 J/g/K, specifically reciting all 0.05 J/g/K increments within the specified ranges and all ranges formed therein or thereby.

The plurality of fibers and/or the plurality of thermally conductive fibers may comprise any suitable fibers, including monocomponent, bicomponent, and/or biconstituent, non-round (e.g., shaped fibers, including but not limited to fibers having a trilobal cross-section, and capillary channel fibers). The fibers can be of any suitable size. The individual fibers may, for example, have major cross-sectional dimensions (e.g., diameter for round fibers) ranging from 0.1-500 microns. Fiber size can also be expressed in denier, which is a unit of weight per length of fiber. The size of the individual fibers may, for example, range from about 0.1 denier to about 100 denier. The plurality of fibers may be a mixture of different fiber types, differing in such features as chemistry (e.g., PE and PP), components (mono- and bi-), and shape (i.e. capillary channel and round). The fibers may have any suitable deniers or denier ranges and/or fiber lengths or fiber length ranges.

The plurality of fibers and/or the plurality of thermally conductive fibers may comprise bicomponent fibers. The bicomponent fibers may each comprise a core and a sheath. The core and/or the sheath may comprise the filler and/or a polymer. The weight ratio between the core and the sheath may be from about 40:60 to about 60:40, from about 45:55 to about 55:45, or about 50:50. Alternatively, the bicomponent fibers can be of different types including side-side, eccentric core-sheath, "islands in a sea," splittable pie, and hollow-center pie.

FIG. 16 illustrates a schematic diagram of a forming machine 310 used to make a nonwoven material 312 as described herein. To make a nonwoven material, the forming machine 310 is shown as having a first beam 320 for producing first coarse fibers 335 (e.g., spunbond fibers), an optional second beam 321 for producing intermediate fibers 327 (e.g., meltblown fibers), a third beam 322 for producing fine fibers 331 (e.g., N-fibers), and a fourth beam 323 for producing second coarse fibers 324 (e.g., spunbond fibers). The forming machine 310 may comprise an endless forming belt 314 which travels around rollers 316, 318 so the forming belt 314 is driven in the direction as shown by the arrows 314. If the optional second beam 321 is utilized, it may be positioned intermediate the first beam 320 and the third beam 322 (as illustrated), or may be positioned intermediate the third beam 322 and the fourth beam 324, for example. Rolls 338 and 340 may form a nip to bond or calender bond the fibers in the multiple layers together to form the nonwoven material. Element 336 may be a layer of spunbond fibers. Element 328 may be a layer of intermediate fibers, spunbond fibers, or fine fibers. Element 332 may be a layer of intermediate fibers, spunbond fibers, or fine fibers. Element 325 may be a layer of spunbond fibers. Each of the layers of fibers may be formed to grow fibrils extending outwardly therefrom after a predetermined period of time under ambient conditions, as discussed in further detail below.

FIG. 17 illustrates a cross-sectional view of an SNS nonwoven material or an SMS nonwoven material at a calender bond site 368. Fibrils may grow out of the calender bond site 368 after a predetermined period of time under ambient conditions. The spunbond, intermediate, and fine fibers may be of single component or bicomponent or polymer blend type.

Referring to FIGS. 17 and 18, the nonwoven material 312 may comprise a first nonwoven layer 325, a second nonwoven layer 332, and a third nonwoven layer 336. The bond site 368 may have a bond area. The second nonwoven layer 332 may be disposed intermediate the first nonwoven layer 325 and the third nonwoven layer 336. Also, the first nonwoven layer 325, the second nonwoven layer 332, and the third nonwoven layer 336 may be intermittently bonded to each other using any suitable bonding process, such as a calendering bonding process, for example. The nonwoven material 312 may not comprise a film. The nonwoven material 312 may comprise a spunbond layer, which may correspond to the first nonwoven layer 325, an N-fiber layer or intermediate layer, which may correspond to the second nonwoven layer 332, and a second spunbond layer, which may correspond to the third nonwoven layer 336. The nano-fiber layer may instead be a meltblown fiber layer. Any of the layers may comprise cotton.

Figure 19:
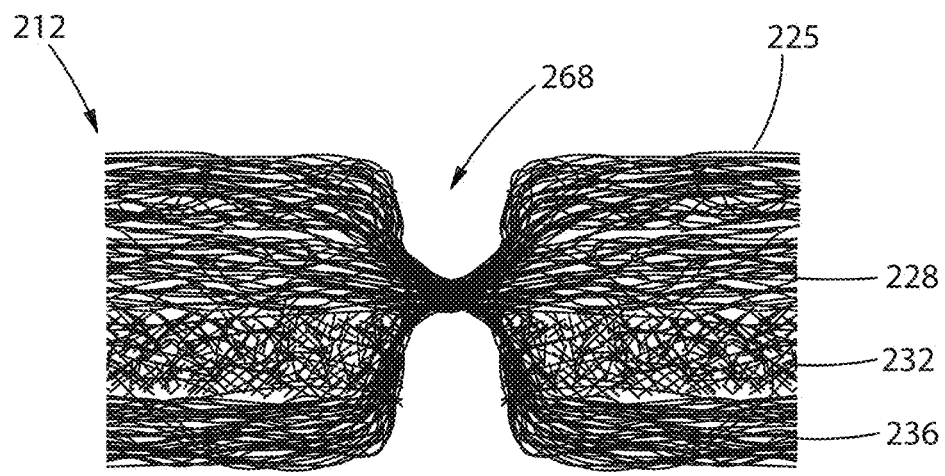
FIG. 19 is a cross-sectional view of a nonwoven material in a four layer configuration, as described herein.
Figure 20:
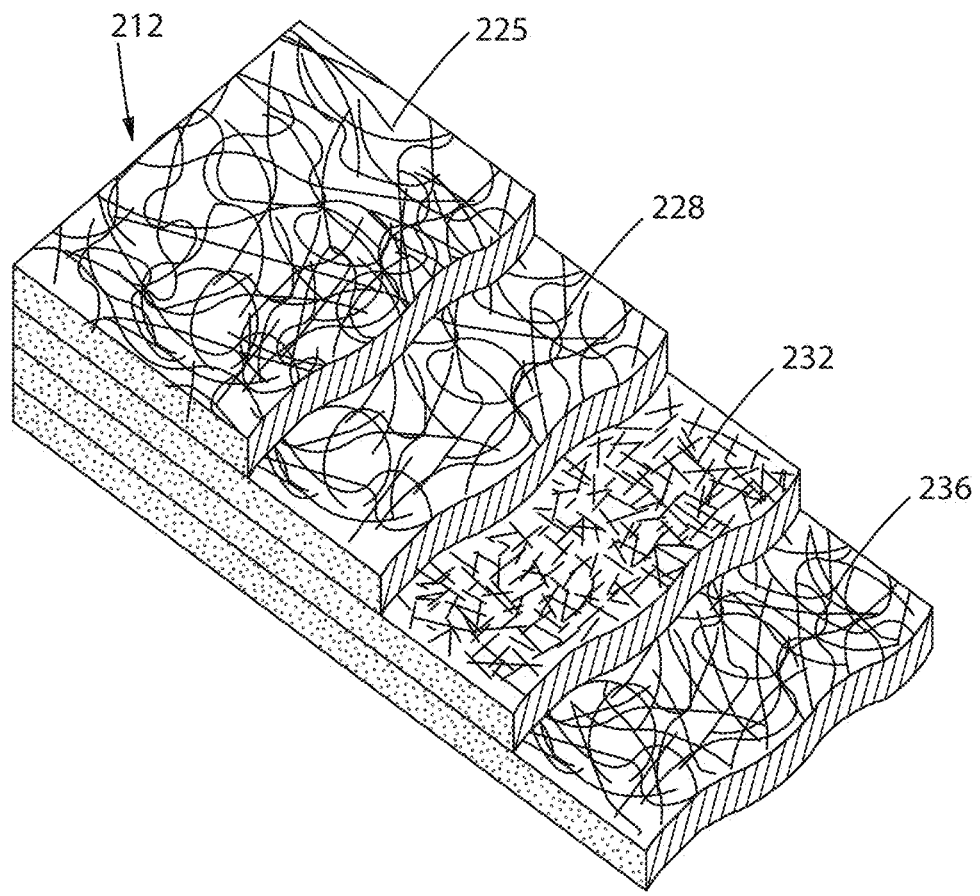
FIG. 20 is a perspective view of the nonwoven material of FIG. 19 with various portions of nonwoven layers cut away to show the composition of each nonwoven layer, as described herein.

Referring to FIGS. 19 and 20, a nonwoven material 212 may comprise a first nonwoven layer 225, a second nonwoven layer 232, a third nonwoven layer 236, and a fourth nonwoven layer 228. A bond site 268, such as a calender bond site, is illustrated in the nonwoven material 212. The bond site 268 has a bond area. The first nonwoven layer 225, the second nonwoven layer 232, the third nonwoven layer 236, and the fourth nonwoven layer 228 may be intermittently bonded to each other using any suitable bonding process, such as a calendering bonding process, for example. The nonwoven material 212 may not comprise a film. The nonwoven material 212 may comprise a spunbond layer, which may correspond to the first nonwoven layer 225, a meltblown layer or fine fiber layer, which may correspond to the fourth nonwoven layer 228, a fine or N-fiber layer or a meltblown layer, which may correspond to the second nonwoven layer 232, and a second spunbond layer, which may correspond to the third nonwoven layer 236. Other configurations of nonwoven materials are envisioned and are within the scope of the present disclosure, such as a nonwoven material comprising one or more spunbond layers, one or more meltblown or intermediate layers, and/or one or more fine or N-fiber layers, for example.

The plurality of fibers and/or the plurality of thermally conductive fibers described herein can be formed from many processes including air laying processes, wetlaid processes, meltblowing processes, spunbonding processes, and carding processes. The plurality of fibers and/or the plurality of thermally conductive fibers in the nonwoven materials can then be bonded via spunlacing processes, hydroentangling, calendar bonding, through-air bonding and resin bonding. The nonwoven material may also comprise needle punched materials.

The nonwoven materials described herein may be formed of a plurality of nonwoven layers arranged in various combinations and permutations of a plurality of spunbond, meltblown, and N-fiber layers, including but not limited to SMS, SMMS, SSMMS, SMMSS, SMN, SNS, SMNMS, SMMNMS, SSMMNS, SSNNSS, SSSNSSS, SSMMNNSS, SSMMNNMS, and the other suitable variations. One or more of the various layers may comprise the fillers described herein.

Figure 21:
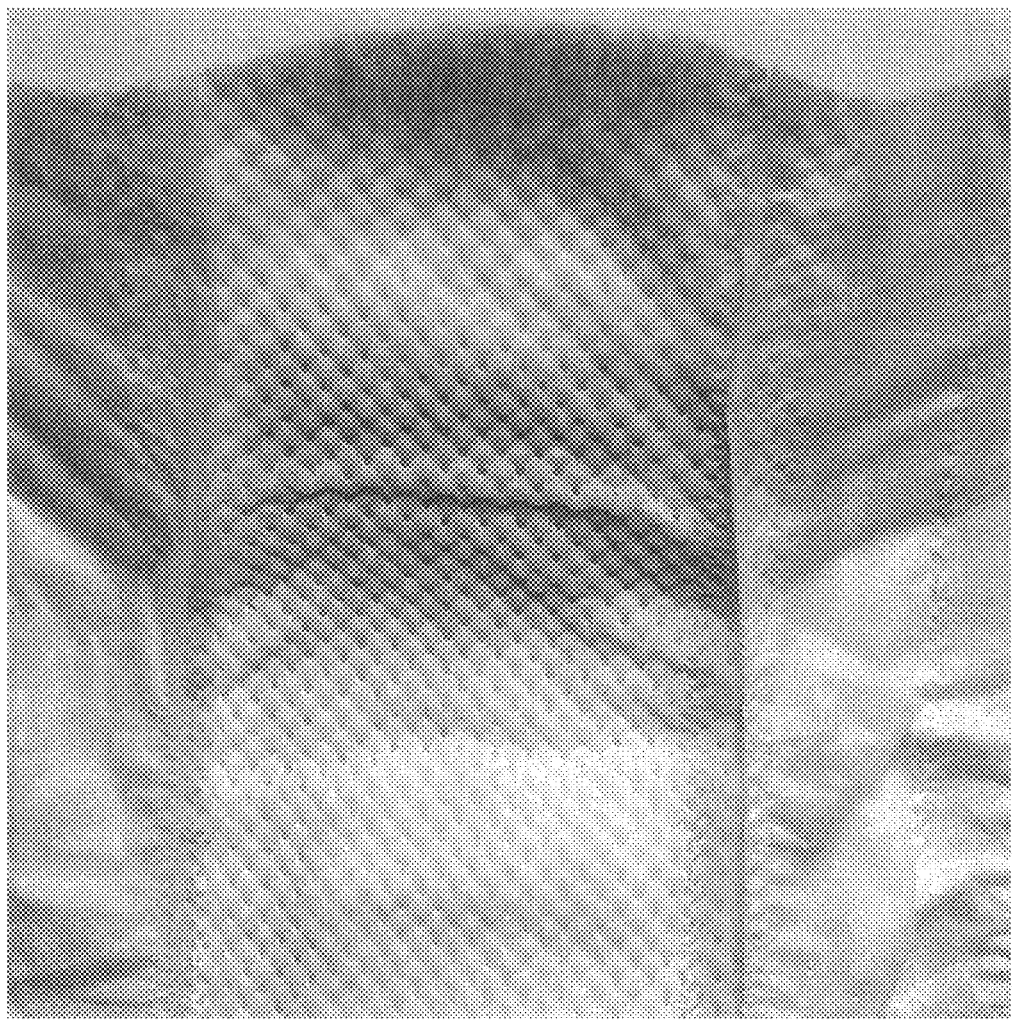
FIG. 21 is an enlarged top view of a portion of a nonwoven material, as described herein.
Figure 22:
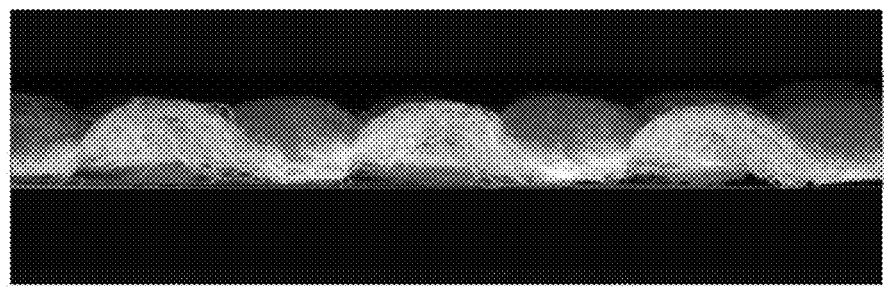
FIG. 22 is a cross-sectional view of a nonwoven material, as described herein.

Examples of apertured and textured materials to which the present disclosure could apply are illustrated in FIGS. 21 and 22. Further details regarding these materials are found in U.S. Patent Publication No. 2015/0250662.

Figure 23:
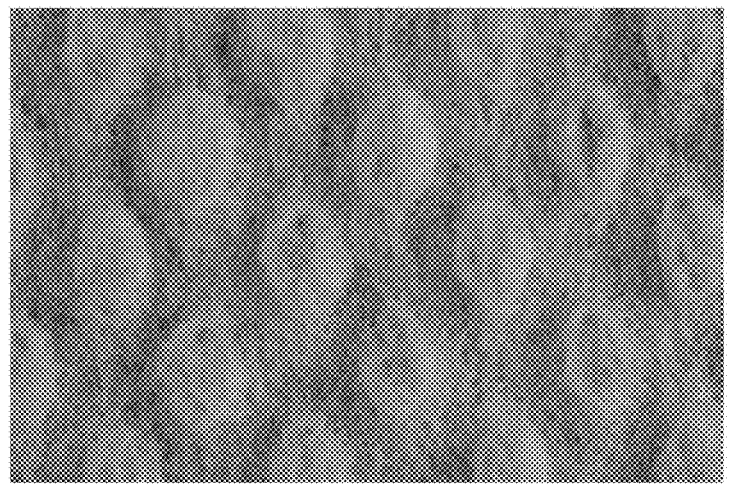
FIG. 23 is a plan view photomicrograph showing one side of a nonwoven material having three-dimensional deformations formed therein, with the protrusions oriented upward, as described herein.
Figure 24:
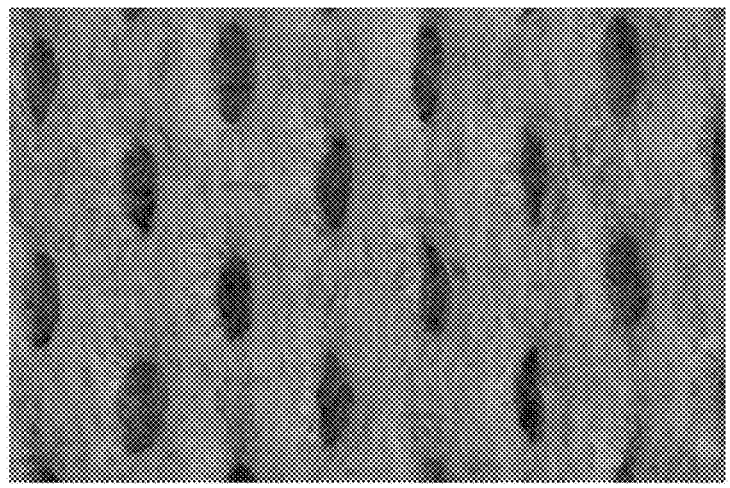
FIG. 24 is a plan view photomicrograph showing the other side of a nonwoven material similar to that shown in FIG. 23, with the openings in the nonwoven material facing upward, as described herein.
Figure 25:
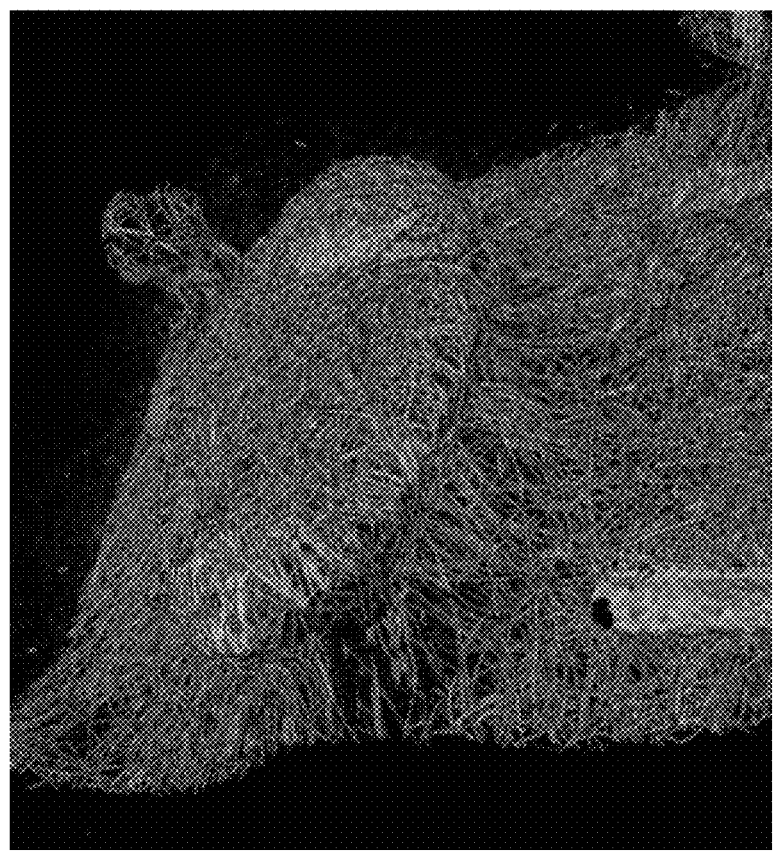
FIG. 25 is a Micro CT scan image showing a perspective view of a protrusion in a single layer nonwoven material, as described herein.

Additional examples of apertured and textured materials to which the present disclosure could apply are illustrated in FIGS. 23-25. Further details regarding these materials are found in U.S. Patent Publication No. 2016/0074250.

Packages

Absorbent articles comprising the nonwoven materials described herein may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages comprising the absorbent articles described herein may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 26:
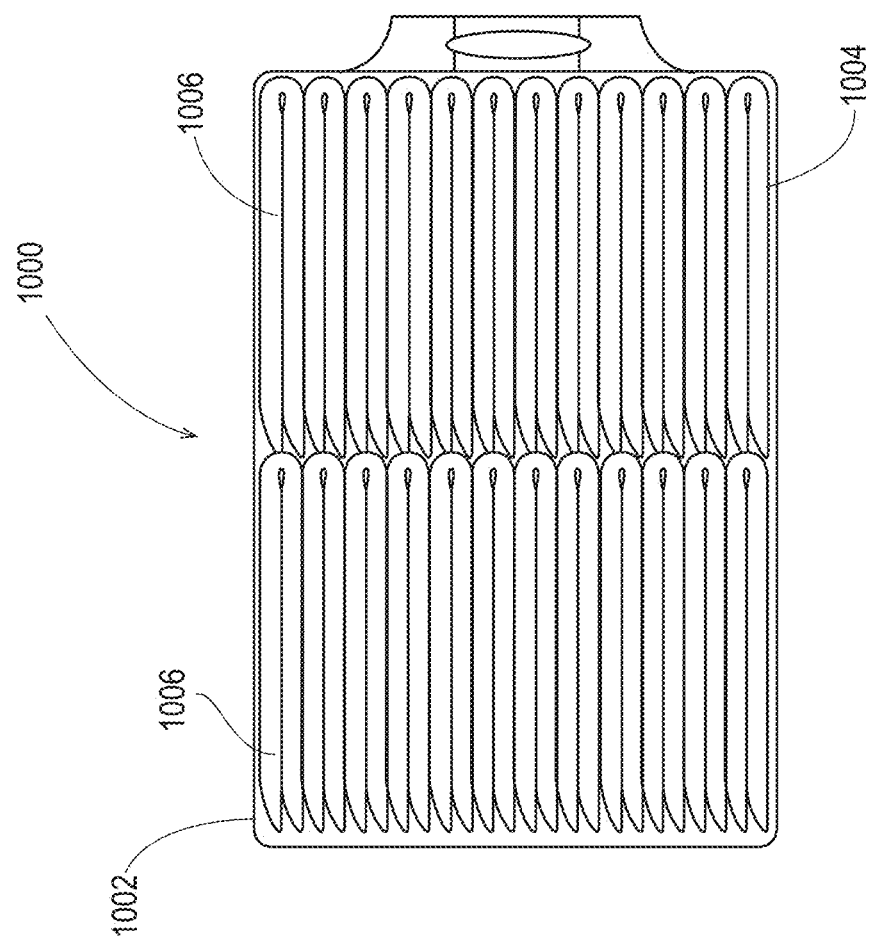
FIG. 26 is a side view of an example package comprising a plurality of absorbent articles, as described herein, wherein the side packaging is transparent.

FIG. 26 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Thermal Conductivity Test Method

The Thermal Conductivity Parameter of a nonwoven material present in an absorbent article is determined using ASTM E1530-11, which is a standard method for measuring thermal transmission through materials using a guarded heat flow meter as described therein. All measurements are done in an environment of 50±2% relative humidity and 23±2° C., and all samples are equilibrated in this same environment for at least twelve hours prior to testing.

Sample Preparation:

The specimen used in the Thermal Conductivity Method is a circular sample disk of nonwoven material 40 mm in diameter and 1.5 mm thick, and this sample disk is made by consolidating of a circle cut from nonwoven material under pressure and at elevated temperature. To create this sample disk, a circular specimen of the nonwoven material of interest 40 mm in diameter and centered at the intersection of the longitudinal and lateral centerlines of the absorbent article is removed. The circle of nonwoven material is then compressed under 70 bar of pressure at 300° C. to create a solid disk of nonwoven material with parallel faces 1.5 mm in thickness. The disk is afterward trimmed to 40 mm in diameter if its lateral extent is increased during the consolidation process. (The basis weight of a single nonwoven material collected from one absorbent article may not be sufficient to provide enough to achieve the specified disk thickness. In this case, multiple equivalent circles are removed from multiple articles and are stacked before compression such that a finished, solid disk 1.5 mm in thickness, results.)

Test Procedure:

The guarded heat flow meter is prepared and calibrated with reference materials as described in ASTM E1530-11. The temperatures of the upper and lower plattens are set such that the temperature difference across the sample is not less than 3° C. and that the arithmetic mean of their set-point values is 30° C. The sample disk is introduced into the guarded heat flow meter and the measurement is performed.

Analysis is performed as specified in the "Analytical Method" described in section 11.2.2 of ASTM E1530-11. The resulting value for thermal conductivity, expressed in units of watts per meter per Kelvin (W m$^{-1}$ K$^{-1}$) to three significant figures, is defined as the Thermal Conductivity Parameter.

Specific Heat Capacity Test Method

The Specific Heat Capacity Parameter is determined using ASTM E1269-11, which is a standard method for determining specific heat capacity by differential scanning calorimetry (DSC). All measurements are done in an environment of 50±2% relative humidity and 23±2° C., and all samples are equilibrated in this same environment for at least twelve hours prior to testing.

A specimen of nonwoven material to be tested is 10 mg in mass and is taken from the intersection of the longitudinal and lateral centerlines of the absorbent article. After performing the specified calibration with synthetic sapphire, the sample nonwoven material is introduced into the DSC, and the measurement and analysis is performed. Specific Heat Capacity Parameter is defined as the specific heat capacity output of the method at 30° C. and is reported in units of Joules per gram per Kelvin ($J\ g^{-1}\ K^{-1}$) to three significant figures.

Particle Size Distribution Method

The particle size distribution is determined using a laser scattering particle size distribution analyzer. A suitable laser scattering particle size distribution analyzer can include a Horiba LA-950V2 (available from Horiba, Ltd., Kyoto, Japan). In this method, the principles of Mie scattering theory (and Fraunhofer approximation where applicable) are used to calculate the size and distribution of particles suspended in a liquid. Results are normally displayed on a volume basis.

Samples are prepared by vortexing for 30 seconds with a Vortex Genie 2 to ensure there is no residue in the bottom of the sample vial. 200 mL of deionized (DI) water (or another appropriate solvent to enable particle dispersion/suspension) is added into the instrument reservoir and analyzed as a blank sample. A disposable micro pipet is used to dispense enough sample into the DI water (or another appropriate solvent to enable particle dispersion/suspension) in the instrument until the Transmittance is reduced from 100 down to 90±2%, approximately 250 μL. Results are reported as D50.

In-Bag Stack Height Test Method

The in-bag stack height of a package of absorbent articles is determined as follows:

Equipment:

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure:

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 26). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the nonwoven materials have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a nonwoven material, wherein the nonwoven material comprises a plurality of fibers, wherein at least some of the plurality of fibers comprise a filler, wherein the plurality of fibers have a Thermal Conductivity of at least 0.25 W/m/K, and wherein the filler has a lamella shape and an aspect ratio of from about 5 to about 150.

2. The absorbent article of claim 1, wherein the filler is selected from the group consisting of boron nitride, talc, zinc oxide, and combinations thereof.

3. The absorbent article of claim 2, wherein the nonwoven material is white.

4. The absorbent article of claim 1, wherein the plurality of fibers on average comprise from about 1% to about 40% of the filler by weight of the nonwoven material.

5. The absorbent article of claim 1, wherein at least some of the plurality of fibers comprise a filler selected from the group consisting of boron nitride, graphene, carbon nanotubes, carbon, talc, zinc oxide, and combinations thereof.

6. The absorbent article of claim 1, wherein the plurality of fibers have a Thermal Conductivity of at least 0.3 W/m/K.

7. The absorbent article of claim 1, wherein the filler has a specific surface area of from about 15 $m^2/g$ to about 60 $m^2/g$, as measured according to BET method ISO 9277.

8. A package comprising a plurality of the absorbent articles of claim 1, wherein the package has an In-Bag Stack Height of less than 95 mm.

9. The absorbent article of claim 1, wherein the plurality of fibers have a Heat Capacity from about 0.5 J/g/K to about 2 J/g/K.

10. The absorbent article of claim 1, wherein the plurality of fibers comprise a plurality of thermally conductive fibers, wherein the plurality of thermally conductive fibers are bicomponent fibers, wherein the plurality of thermally conductive fibers each comprise from about 10% to about 30% of the filler by weight of the plurality of thermally conductive fibers, and wherein the plurality of thermally conductive fibers each comprise from about 70% to about 90% of a polymer by weight of the plurality of thermally conductive fibers.

11. An absorbent article comprising a nonwoven material, wherein the nonwoven material comprises a plurality of fibers, wherein the plurality of fibers on average comprise from about 4% to about 35%, by weight of the nonwoven material, of a filler selected from the group consisting of boron nitride, graphene, carbon nanotubes, carbon, talc, zinc oxide, and combinations thereof, wherein the plurality of fibers have a Thermal Conductivity of at least 0.25 W/m/K, wherein the plurality of fibers have a Heat Capacity from about 0.5 J/g/K to about 2 J/g/K, and wherein the nonwoven material is textured and/or apertured.

12. The absorbent article of claim 11, wherein the absorbent article is a diaper.

13. The absorbent article of claim 12, wherein the diaper comprises:
   a liquid permeable topsheet;
   a liquid impermeable backsheet;
   an absorbent core positioned at least partially intermediate the topsheet and the backsheet; and
   an outer cover in a facing relationship with the backsheet;
   wherein the topsheet and/or the outer cover and/or the absorbent core comprise the nonwoven material.

14. The absorbent article of claim 11, wherein the plurality of fibers comprise a plurality of thermally conductive fibers, wherein the plurality of thermally conductive fibers each comprise from about 10% to about 30% of the filler by weight of the plurality of thermally conductive fibers, and wherein the plurality of thermally conductive fibers each comprise from about 70% to about 90% of a polymer by weight of the plurality of thermally conductive fibers.

15. The absorbent article of claim 11, wherein the plurality of fibers have a Heat Capacity from about 0.5 J/g/K to about 2 J/g/K.

16. A diaper or pant comprising a topsheet, an outer cover, and an absorbent core, wherein the topsheet and/or the outer cover comprise a nonwoven material, wherein the nonwoven material comprises a plurality of fibers, wherein the plurality of fibers have a Thermal Conductivity from about 0.25 W/m/K to about 5 W/m/K, wherein the plurality of fibers have a Heat Capacity from about 0.5 J/g/K to about 2 J/g/K, wherein the nonwoven material is white, and wherein the nonwoven material is apertured and/or textured.

17. The diaper or pant of claim 16, wherein at least some of the plurality of fibers comprise a filler, and wherein the filler is selected from the group consisting of boron nitride, talc, zinc oxide, and combinations thereof.

18. The diaper or pant of claim 17, wherein the plurality of fibers comprise a plurality of thermally conductive fibers, wherein the plurality of thermally conductive fibers are bicomponent fibers, wherein the plurality of thermally conductive fibers each comprise from about 10% to about 30% of the filler by weight of the plurality of thermally conductive fibers, and wherein the plurality of thermally conductive fibers each comprise from about 70% to about 90% of a polymer by weight of the plurality of thermally conductive fibers.

19. The diaper or pant of claim 18, wherein the bicomponent fibers each comprise a core and a sheath, wherein the core and/or the sheath comprise the filler.

* * * * *